US00PP16182P3

(12) United States Plant Patent
Farrow

(10) Patent No.: US PP16,182 P3
(45) Date of Patent: Jan. 3, 2006

(54) ***VERONICA* PLANT NAMED 'TICKLED PINK'**

(50) Latin Name: *Veronica spicata*
Varietal Denomination: Tickled Pink

(75) Inventor: Michael Farrow, Earlville, MD (US)

(73) Assignee: CP Delaware, Inc., Wilmington, DE (US)

( * ) Notice: Subject to any disclaimer, the term of this patent is extended or adjusted under 35 U.S.C. 154(b) by 145 days.

(21) Appl. No.: 10/847,325

(22) Filed: May 18, 2004

(65) Prior Publication Data

US 2005/0262605 P1 Nov. 24, 2005

(51) Int. Cl.
*A01H 5/00* (2006.01)

(52) U.S. Cl. ..... Plt./251

(58) Field of Classification Search ..... Plt./251
See application file for complete search history.

*Primary Examiner*—Anne Marie Grunberg
*Assistant Examiner*—Annette H Para
(74) *Attorney, Agent, or Firm*—Burns, Doane, Swecker & Mathis, LLP

(57) ABSTRACT

A new and distinct *Veronica spicata* cultivar is provided that is well suited for providing attractive ornamentation in flower gardens. The plant is free-flowering and forms attractive bubblegum pink-colored racemes. A vigorous semi-prostrate growth habit is displayed. Durable long ovate to lanceolate leaves are formed. The plant commonly flowers on a substantially continuous basis from early July to mid-September.

2 Drawing Sheets

Botanical/commercial classification: *Veronica spicata*/ *Veronica* Plant.
Varietal denomination: cv. 'Tickled Pink'.

SUMMARY OF THE INVENTION

The new *Veronica* Plant (i.e., Spike Speedwell plant) of the present invention was discovered during 2003 at Holly Hill Farms, Earlville, Md., U.S.A., while growing among a population of plants of the *Veronica spicata* 'Goodness Grows' cultivar (non-patented in the United States). This new plant is believed to be a spontaneous whole plant mutation of unknown causation of the 'Goodness Grows' cultivar, and displays a distinctive blossom coloration together with a low growth habit. The new plant has been carefully preserved and evaluated in view of its distinctive combination of characteristics. Had the new cultivar not been discovered and preserved, it would have been lost to mankind.

It was found that the new *Veronica spicata* plant of the present invention displays the following combination of characteristics:

(a) exhibits a vigorous semi-prostrate growth habit, (b) is free-flowering and forms attractive bubblegum pink-colored racemes, (c) forms durable long ovate to lanceolate leaves, and (d) is well suited for providing attractive ornamentation in the landscape.

The new cultivar well meets the needs of the horticultural industry and can be grown to advantage as a perennial garden plant to provide colorful ornamentation. For instance, it can be grown in front of borders, in rock gardens to provide a cascading effect, and in hanging baskets.

Plants of the new cultivar can be readily distinguished from other *Veronica spicata* cultivars including its parent. More specifically, the 'Goodness Grows' cultivar forms dark blue blossoms instead of blossoms having the bubblegum pink-colored coloration of the new cultivar.

The 'Minuet' (non-patented in the United States) and 'Alba' (non-patented in the United States) low-growing cultivars also display different characteristics. These cultivars along with the new cultivar commonly grow well in U.S.D.A. Hardiness Zone Nos. 3 to 8. The 'Minuet' cultivar forms dissimilar grey-green foliage, forms longer flowers of approximately 10 to 15 inches in length, and commonly stops blooming in late Spring. The 'Alba' cultivar forms dissimilar white flowers that are longer and commonly measure approximately 15 inches in length, and commonly blooms only in June and July.

The rooting of cuttings beginning in 2003 has been used to asexually propagate the new cultivar at West Grove, Pa., U.S.A. Rooted liners can be produced in approximately 30 days, and mature fully-grown flowering plants can be produced in approximately 25 weeks in 1½-liter containers. It has been found that the characteristics of the new cultivar are stable and are reliably transmitted from one generation to another. Accordingly, the new cultivar can be asexually reproduced in a true to type manner.

The new cultivar of the present invention has been named 'Tickled Pink'.

BRIEF DESCRIPTION OF THE PHOTOGRAPHS

The accompanying photographs illustrate the new cultivar in color as nearly true as it is reasonably possible to make the same in color illustrations of this nature. The plants were grown in containers at West Grove, Pa., U.S.A.

DETAILED DESCRIPTION

Figure 1:
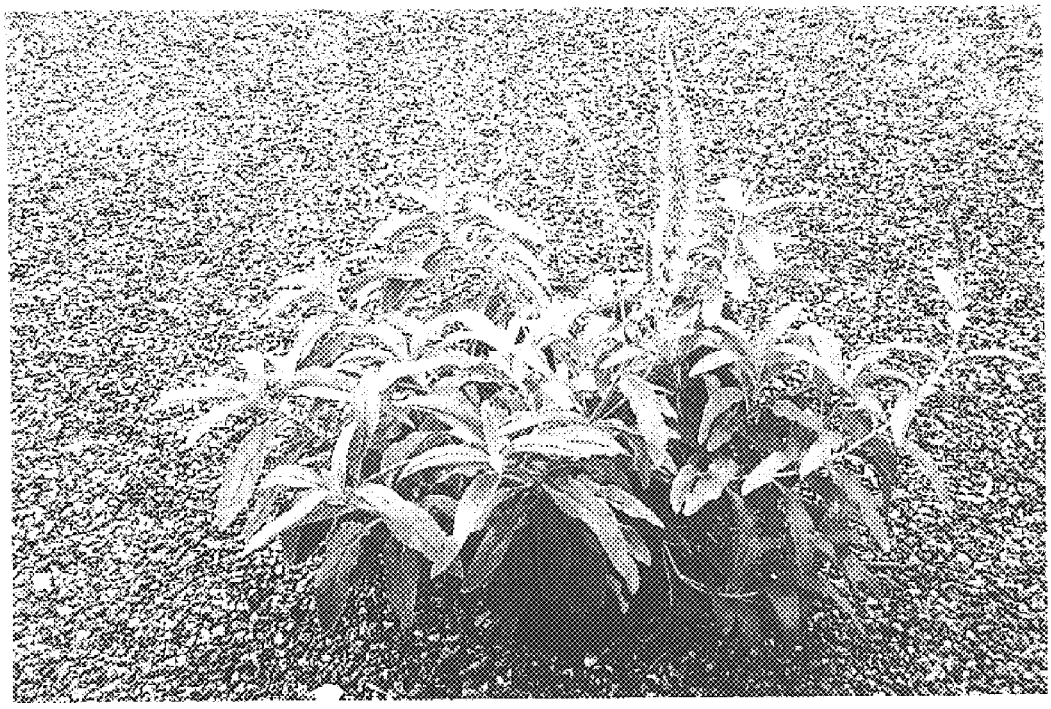
FIG. 1 illustrates a specimen of a typical mature flowering plant of the new cultivar wherein the semi-prostate growth habit is apparent.
Figure 2:
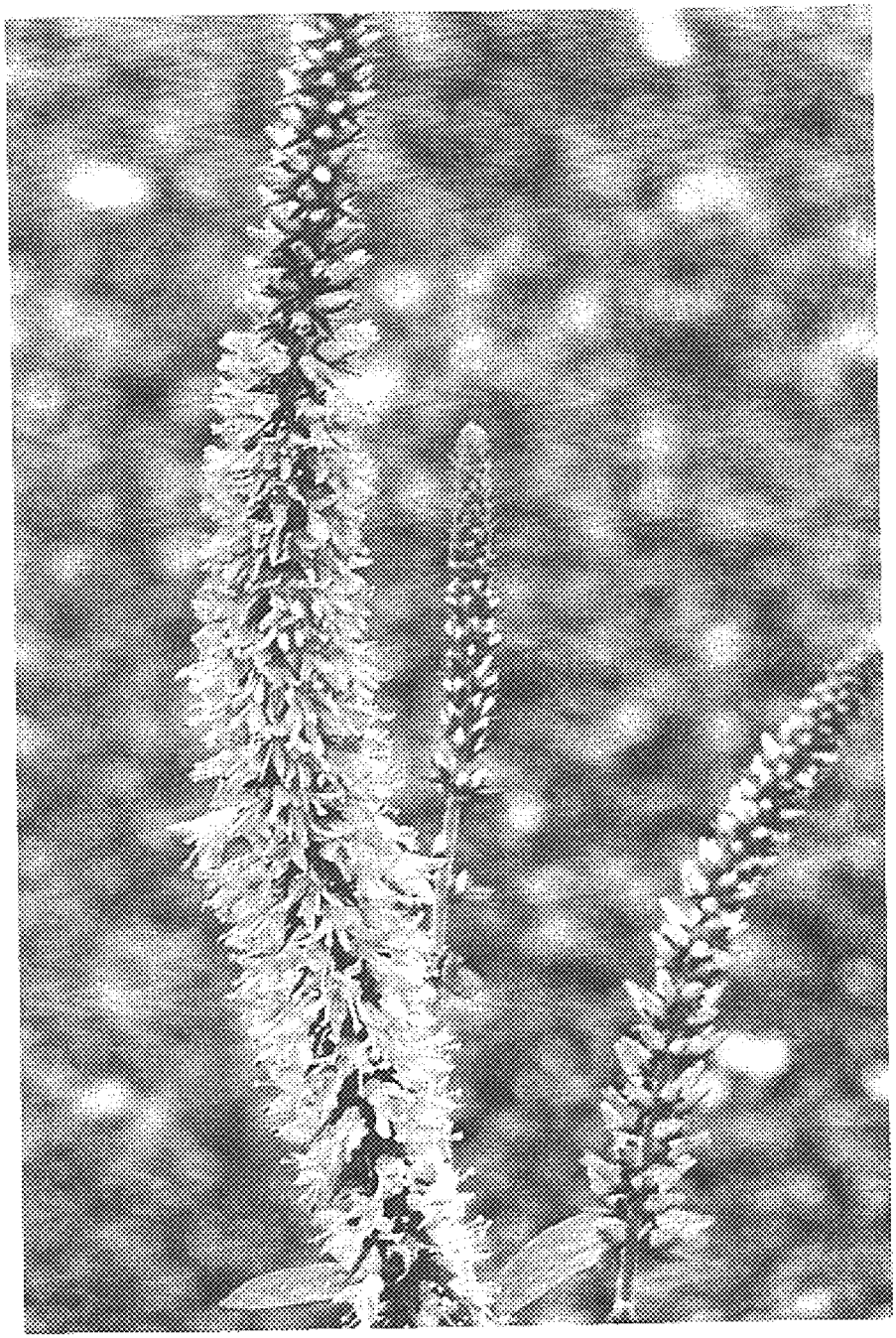
FIG. 2 illustrates a closer view of the flowers of the new cultivar in various stages of development.

The following is a detailed description while observing fully-grown plants of the new cultivar during the spring approximately 25 weeks following the rooting of cuttings. Such plants were grown in containers under greenhouse conditions at West Grove, Pa., U.S.A. The chart used in the identification of color is The R.H.S. Colour Chart of The Royal Horticultural Society, London, England. Common color terms are to be accorded their customary dictionary significance.

Botanical classification: *Veronica spicata*, cv. 'Tickled Pink'.

*Parent.*—*Veronica spicata*, cv. 'Goodness Grows'.

Plant:

*Growth habit.*—Semi-prostate with a mat-type growth.
*Height.*—Approximately 15 cm.
*Spread.*—Approximately 60 cm.
*Vigor.*—Extremely vigorous.
*Branching.*—Freely-branching, commonly with approximately 14 lateral branches.
*Lateral branches.*—Commonly approximately 40 cm in length, approximately 4 mm in diameter, pubescent, and near Green Group 143A to 143C in coloration.
*Internode length.*—Commonly varies from approximately 15 to 45 mm.
*Roots.*—Fine and fibrous.

Foliage:

*Type.*—Simple, durable and long persisting.
*Arrangement.*—Opposite.
*Shape.*—Long narrowly ovate to lanceolate and symmetrical.
*Apex.*—Acuminate.
*Base.*—Attenuate.
*Length.*—Sometimes up to approximately 13 cm.
*Width.*—Commonly approximately 2.5 to 3 cm.
*Texture.*—Glabrous on the upper surface and pubescent on the under surface.
*Color.*—Young Foliage: Yellow-Green Group 144A on the upper and lower surfaces. Mature Foliage: Green Group 137A on the upper surface and Green Group 137C on the lower surface.
*Venation.*—Pinnate, Green Group 137A on the upper surface and Yellow-Green Group 144B in coloration on the lower surface.
*Petiole.*—Commonly approximately 25 mm in length, approximately 4 mm in diameter, smooth in texture, and Yellow-Group 144C in coloration on the upper and lower surfaces.

Inflorescence:

*Time.*—Substantially continuous during the summer from early July to mid-September.
*Type.*—Single arranged in upright racemes that primarily face outwards.
*Buds.*—Elliptic, approximately 4 mm in length, approximately 1.75 mm in diameter, and near Violet-Blue Group 93C and 93D in coloration.
*Quantity.*—Free-flowering, commonly 1 to 5 flowering racemes per lateral branch, and commonly more than 140 open flowers and flower buds per flowering raceme.
*Racemes.*—Approximately 13.5 cm in length and approxiamtely 2 cm in width.
*Corolla configuraion.*—Four-parted, petals fused at base, cupped or campanulate.
*Flower diameter.*—Approximately 6 mm.
*Flower length.*—Approximately 8 mm.
*Petal shape.*—Obovate.
*Petal length.*—Approximately 7 mm.
*Petal width.*—Approximately 3 mm.
*Petal apex.*—Obtuse.
*Petal margin.*—Entire.
*Petal texture.*—Generally smooth and sparsely covered with very short less than 0.1 mm in length pale grayish hairs at the base.
*Petal color.*—Bubblegum pink, near Red-Purple Group 68B on both surfaces.
*Sepal arrangement.*—Four in number, fused at base, campanulate.
*Sepal shape.*—Lanceolate.
*Sepal length.*—Approximately 4 mm.
*Sepal diameter.*—Approximately 2 mm.
*Sepal apex.*—Acute.
*Sepal margin.*—Entire.
*Sepal texture.*—Smooth on both surfaces.
*Sepal color.*—Near Green Group 137A to 137B on both surfaces.
*Stamen number.*—Two.
*Anther shape.*—Reniform and dorsifixed.
*Anther length.*—Approximately 1.5 mm.
*Pollen.*—Present in a moderate to abundant quantity and near Yellow Group 4C in coloration.
*Pistil number.*—One.
*Stigma shape.*—Flattened.
*Stigma color.*—Near Violet-Blue Group 93A.
*Style length.*—Approximately 7 mm.
*Style width.*—Approximately 0.2 mm.
*Style color.*—Near Violet-Blue Group 93A.
*Ovary color.*—Green Group 143C.
*Seed length.*—Approximately 1 mm.
*Seed diameter.*—Approximately 0.5 mm.
*Seed color.*—Dark grayish-brown.
*Fragrance.*—None observed.
*Flower longevity.*—Approximately 6 to 8 days on the plant, and approximately 14 days or more when cut and placed in a vase.
*Peduncle strength.*—Strong.
*Peduncle angle.*—Approximately 45 to 60° from the stem.
*Peduncle length.*—Approximately 1 mm.
*Peduncle diameter.*—Commonly less than 1 mm.
*Peduncle color.*—Near Green Group 137A.

Disease resistance: No particular resistance to pathogens and pests common to *Veronica* plants has been encountered during observations to date.

Plants of the 'Tickled Pink' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Veronica* plant having the following combination of characteristics:

(a) exhibits a vigorous semi-prostrate growth habit,
(b) is free-flowering and forms attractive bubblegum pink-colored racemes,
(c) forms durable long ovate to lanceolate leaves, and
(d) is well suited for providing attractive ornamentation in the landscape;

substantially as illustrated and described.

* * * * *